(12) United States Patent
Baroud et al.

(10) Patent No.: US 6,383,227 B1
(45) Date of Patent: May 7, 2002

(54) FEMORAL NECK ENDOPROSTHESIS FOR AN ARTIFICIAL HIP JOINT

(75) Inventors: Gamal Baroud, Montreal (CA); Klaus Brämer; Reiner Kreissig, both of Chemnitz (DE)

(73) Assignee: aap Implanters AG, Berlin (DE)

( * ) Notice: Subject to any disclaimer, the term of this patent is extended or adjusted under 35 U.S.C. 154(b) by 0 days.

(21) Appl. No.: 09/744,843

(22) PCT Filed: Jul. 28, 1999

(86) PCT No.: PCT/DE99/02318

§ 371 Date: Mar. 20, 2001

§ 102(e) Date: Mar. 20, 2001

(87) PCT Pub. No.: WO00/06054

PCT Pub. Date: Feb. 10, 2000

(51) Int. Cl.$^7$ .................................................. A61F 2/36
(52) U.S. Cl. .............................. 623/23.22; 623/23.26; 623/23.11; 623/23.15
(58) Field of Search ........................... 623/22.11, 23.15, 623/23.21, 23.22, 23.26, 23.27, 23.11, 22.15, 22.4, 22.43, 22.44, 22.46, 23.12, 23.14

(56) References Cited

U.S. PATENT DOCUMENTS

| | | | |
|---|---|---|---|
| 2,947,308 A | * | 8/1960 | Gorman |
| 4,129,903 A | * | 12/1978 | Huggler |
| 4,976,740 A | * | 12/1990 | Kleiner |
| 5,376,125 A | * | 12/1994 | Winkler |
| 5,980,575 A | * | 11/1999 | Albrektsson et al. |

FOREIGN PATENT DOCUMENTS

| | | | |
|---|---|---|---|
| DE | 2724234 A | * | 12/1977 |
| DE | 3017953 A | * | 2/1981 |
| EP | 099167 A | * | 1/1984 |
| WO | WO-86/03962 A | * | 7/1986 |
| WO | WO-89/11837 A | * | 12/1989 |

* cited by examiner

*Primary Examiner*—Jeffrey A. Smith
(74) *Attorney, Agent, or Firm*—Cohen, Pontani, Lieberman & Pavane

(57) ABSTRACT

A femoral neck endoprosthesis for an artificial hip joint, having an adapter for accommodating the joint ball, a support ring for guiding the adapter on the proximal side of the femur, and a support bearing for guiding the adapter on the lateral side of the femur. The aim of the invention is to increase the strength of the bone tissue for a prosthesis. To this end, the prosthesis is configured in such a way that the adapter is provided with a support shoulder and with a shaft which penetrates the femur approximately along the extended axis of the femoral neck. The support ring is mounted on the proximal side of the femur only with its support surface. An axial stop for the support shoulder and a bore for the shaft are arranged on the support ring for guiding the adapter. The bore is laterally offset in relation to the support surface. The support bearing is fixed only on the lateral side of the femur and the guide bore for the shaft can be aligned with the axis of the adapter.

12 Claims, 2 Drawing Sheets

FEMORAL NECK ENDOPROSTHESIS FOR AN ARTIFICIAL HIP JOINT

BACKGROUND OF THE INVENTION

1. Field of the Invention

The invention relates to a femoral neck endoprosthesis for an artificial hip joint, consisting of an adapter for accommodating the joint ball, a support ring for axially and radially guiding the adapter on the proximal side of the femur, and a support bearing for guiding the adapter on the lateral side of the femur.

2. Discussion of the Prior Art

Such femoral neck endoprosthesis are already known in a wide variety of forms.

For example, DE 27 24 234 A1 discloses such a prosthesis. The adapter accommodating the joint ball is provided with a support shoulder, and a shaft protrudes far into the femur. The approximately conical support shoulder sits on a support ring which is fixed on the femoral neck by the form of its outer edge. On the lateral side of the femur, a support bearing covering a large surface area is screwed on from the outside.

Through this support bearing, a long screw with a long shaft which penetrates the femur is fixed laterally to the adapter by means of a thread. This screw has a long guide section which sits with a form-fit in a corresponding long bore in the shaft of the adapter. This long screw braces the adapter at one end against the support bearing and at the other end against the support ring. Without this axial bracing, the adapter is not able to reliably introduce the considerable loads into the femur.

Such a prosthesis has a number of disadvantages. The large surface areas of the cortical substance enclosed by parts of the prosthesis are no longer adequately supplied after the prosthesis has been fitted. The properties of these areas of the cortical substance alter in an adverse manner. The cortical substance can no longer take up the forces which normally occur. The functional capacity of such a prosthesis is thus considerably limited in time.

The permanent bracing of the femur between support bearing and support ring leads to a permanent deformation of the bone and therefore to a loosening of the prosthesis. The permanent loading of the bone as a result of said bracing leads to damage of the cortical substance, above all at the pressure surfaces. The resistance of the cortical substance diminishes. After a relatively short time, the functional capacity of the prosthesis in no longer guaranteed.

A similar prosthesis is also described in EP 207 985 B1. The support body assigned to the adapter is in this case configured as a prismatic body which is introduced with a form-fit into a corresponding recess prepared in the femur. This prismatic support body ensures that the forces normally acting on the prosthesis via the joint ball are transmitted into the approximately perpendicular parts of the cortical substance over a relatively large surface area and at an optimum angle of transmission.

However, a disadvantage in this case is once again that the prismatic support body can only fulfill its function if it is braced against a support bearing on the other side, i.e. the lateral side, of the femur by means of a screw connection.

The disadvantages described earlier are also present in this design. In the case of this solution, a further considerable disadvantage lies in the great loss of bone substance. Under the effect of the normal loads and the necessary bracing force, the wedge-shaped support body leads to additional deformation of the femur.

The rigid connection between the support bearing and the adapter via a long fitted sleeve causes additional damage to the femur. The useful life of such a prosthesis is thus likewise considerably limited.

A further alternative design was proposed in a thesis by Mr Garnal Baroud at the Technical University of Chemnitz (defended on Dec. 12, 1997). The adapter is in this case likewise provided with a support shoulder. At its outer end, the support shoulder merges into a long shaft which extends to the other side of the femur and which preferably has a limited elasticity.

The adapter of said configuration is introduced into a guide sleeve surrounding the shaft and the support shoulder. This guide sleeve consists of a support ring, a support bearing, and a sleeve-like elastic connection between the two support elements.

The support ring has, in a rotationally symmetrical recess, an axial stop for the support shoulder and a bore for the shaft of the adapter. Provided at the other end of the guide sleeve is the so-called support bearing which is held with a radial form-fit in a corresponding bore in the lateral cortical substance. The support ring and the support bearing are connected to each other with limited elasticity via the sleeve-like, tightly wound spiral spring of relatively large diameter.

This assembled guide sleeve is introduced from the proximal side into a correspondingly large bore in the femur. The radially directed flange of the support ring lies, transversely with respect to the axial direction of the guide sleeve, on a correspondingly worked bearing surface of the cortical substance.

The adapter which is then fitted is held and radially guided in this guide sleeve with its support shoulder on the stop surface in the support ring.

By means of this arrangement of the guide sleeve and the limited elasticity of the shaft of the adapter, and also by means of a spring washer which can be inserted, if necessary, between the adapter and the guide sleeve, movements within the prosthesis and possible peak loads can be taken up and transmitted into the femur over a large surface area.

A considerable disadvantage has proven to be that under these conditions a relatively large proportion of the forces acting transversely with respect to the axis of the adapter are transmitted into the relatively soft spongy substance of the femur, at least until such time as the prosthesis has become incorporated. The primary stability of the prosthesis is thereby limited.

A further disadvantage lies in the relatively high production outlay and the relatively large amount of foreign material which has to be introduced into the femur. Another negative factor is that a relatively large part of the femur has to be removed. However, the decisive disadvantage lies in the required connection between the support ring and the support bearing. The initial press-fit of the support bearing in the lateral cortical substance and the later incorporation of this support bearing lead, in this embodiment too, to stresses in the femur and at the contact points between the femur and the prosthesis.

These stresses still lead to damage of the bone tissue—albeit to a far lesser extent than in the prostheses described in the introduction—and therefore contribute to reducing the useful life of the prosthesis.

SUMMARY OF THE INVENTION

It is therefore an object of the present invention to make available a femoral neck endoprosthesis which avoids bracing the femur for the purpose of securing the elements of the prosthesis and during normal loading. The invention is intended to create conditions in which local peak loads can be reduced within the prosthesis body.

The contact surfaces between the prosthesis and the supporting parts of the cortical substance are to be configured in such a way that the natural supply to the bone tissue is guaranteed during the required period of functioning of the prosthesis.

The inventive femoral neck endosthesis includes an adapter for accommodating the joint ball, a support ring for axially and radially guiding the adapter on a proximal side of the femur, and a support bearing for guiding the adapter on a lateral side of the femur. The adapter has a support shoulder directed toward the femur and a shaft which penetrates the femur approximately along an extended axis of the femoral neck. The support ring is mounted only on the proximal side of the femur and has a flange support surface mounted on a worked bearing surface of the proximal cortical substance of the femur and a hub mounted inside the femur. The support ring further has an axial stop for the support shoulder of the adapter and a bore for the shaft of the adapter so as to guide the adapter. The bore is laterally offset in relation to the support surface. The support bearing is fixed only on the lateral side of the femur, substantially on the lateral cortical substance. The support bearing has a guide bore for the shaft of the adapter, which guide bore has an active access that is lineable with the axis of the adapter.

As a result, in the end, of the absence of a rigid connection between the support ring and the support bearing, loads are introduced into the proximal cortical substance, in the same way as under natural conditions. Bracing of the femur transversely with respect to its longitudinal axis is completely avoided. The forces are predominantly introduced into the stable proximal cortical substance. Even under unfavorable load conditions, none of the feared tensile forces occur at the contact points between the prosthesis and the femur. The narrow contact surfaces can be reached at all times by the body fluids supplying the bone. Disintegration of the bone structure can therefore be avoided for much longer.

Because of the omission of a mechanical connection between the proximal and lateral cortical substance, the femur as a whole can deform in a natural way. This contributes considerably to preserving the functions of the bone tissue.

In view of the tendons and muscles present in the human body in this area, it is not necessary to provide additional axial securing of the adapter in the support ring and in the support bearing against movement in the proximal direction.

The prosthesis is easy to manufacture and can also be adapted without difficulty to different sizes and shapes of femur.

The prosthesis possesses the necessary primary stability.

The configuration of the support surface of the adapter and of the support ring with a suitable central cone angle ensures that the load normally applied via the joint ball can be introduced under optimum conditions into the supporting cortical substance. In the event of excessive loading, additional safety is afforded by the bore in the support ring.

The support surface of the support ring on the proximal cortical substance permits optimum introduction of the normal load along the femur. The support ring itself is elastic in the area between the support shoulder of the adapter and the bearing surface of the cortical substance. It can therefore also reduce the unavoidable peak loads.

In addition to the desired elasticity, the support ring can have a substantially nonelastic inner conical flange and an axially elastic spring ring between the support shoulder of the adapter and the inner cone of the conical flange to ensure a certain damping of peak loads as forces are introduced into the femur.

In another embodiment of the invention the support bearing penetrates the lateral cortical substance of the femur approximately perpendicular to its surface and with a form fit. The support bearing furthermore has a bore for guiding the shaft of the adapter. The axes of the bore is inclined in relation to the axis of the support bearing by an angle between 5° and 30°. In yet another embodiment the support bearing is provided with profiles for turning the support bearing in the cortical substance. The bore is aligned with the probable position of the axis of the shaft of the adapter and has a dome shape. These embodiments of the support bearing permit a low-weight design of the support bearing with a very small contact surface against the supporting cortical substance. The cortical substance is adequately supplied as far as the center of the bearing surface. The axis of the bore guiding the shaft of the adapter can in this case be aligned from the outset to the desired angle. The dome shape of the bore permits a certain correction in situ.

In yet another embodiment the support bearing consists of an outer guide ring with a spherical inner guide surface, and a spherical slide ring which can be fitted in the guide ring and which has a bore for the shaft of the adapter. This design of the support bearing permits adaptation of the bore in a greater range with optimum mobility of the shaft in the bore.

In still another embodiment a detachable axial bearing is assigned to the outer end of the shaft. The axial bearing can be a threaded bushing whose external diameter penetrates the bore in the support bearing with play. The threaded bushing has axially directed stops on the outside and can be axially adjusted at the end of the shaft by a screw connection and can be fixed in the adjusted position. This arrangement of the axial bearing and its design ensure that the functional capacity of the prosthesis is maintained even under extreme conditions. However, it is important here that adequate play is at all times present between the axial stops of the bushing and the support bearing and that the bushing does not come away from the shaft.

BRIEF DESCRIPTION OF THE DRAWINGS

The invention will be described in more detail on the basis of illustrative embodiments and with reference to the attached drawings, in which:

FIG. 5 shows a support bearing designed as a swinging slide bearing.

DETAILED DESCRIPTION OF THE PREFERRED EMBODIMENTS

Figures 1, 2:
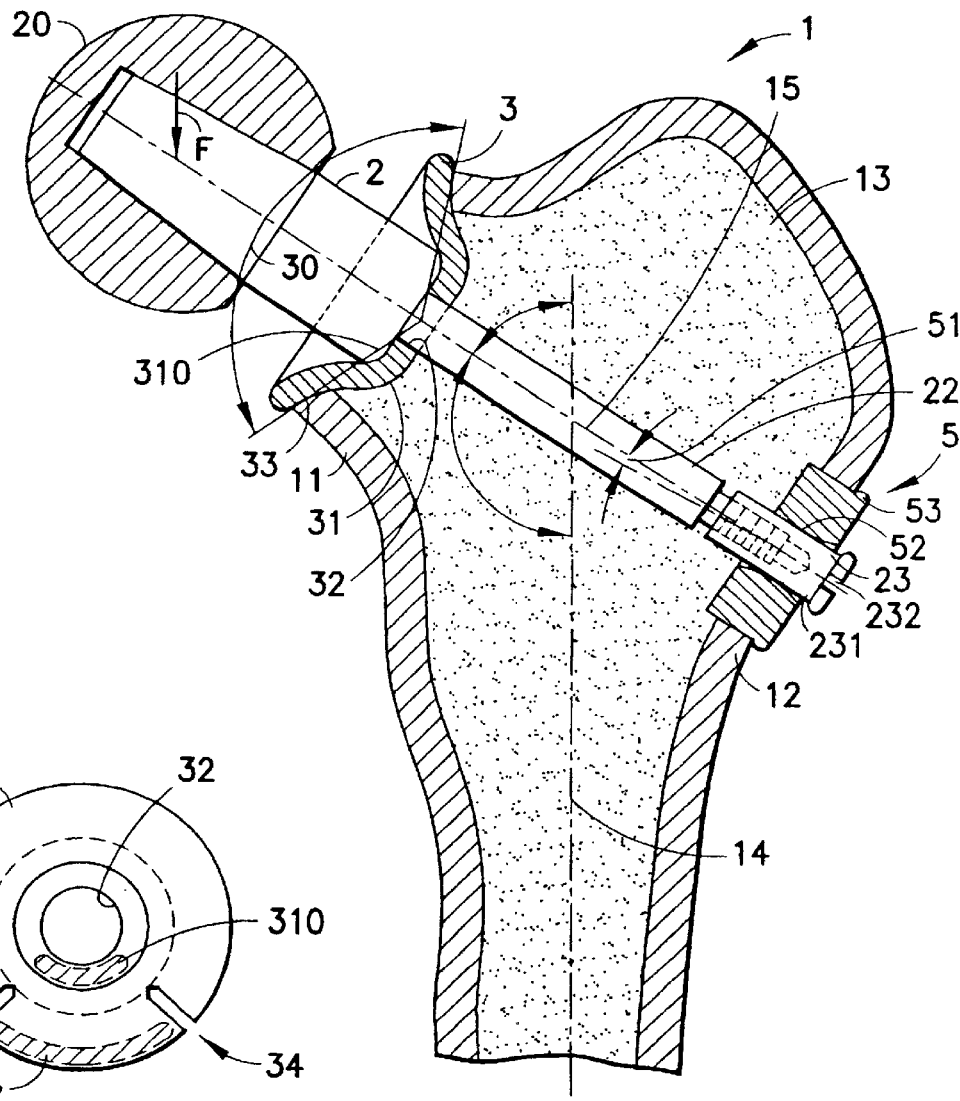
FIG. 1 shows a cross section through the head of a femur, with the femoral neck endoprosthesis fitted.
FIG. 2 shows a view of the support ring along its axis.

A femoral neck endoprosthesis is fitted into the femur 1 at an angle 16 to the longitudinal axis 14 of the thigh bone. The axis 15 of the femoral neck endoprosthesis corresponds approximately to the axis of a healthy femoral neck. The angle 16 (FIG. 1) in this case is between 40° and 60°.

The femoral neck endoprosthesis consists of an adapter 2 which accommodates the joint ball 20 on a slightly conical section in its head area. Close below this joint ball 20, a support shoulder 21 is provided on the adapter 2.

Immediately behind the support shoulder 21, the adapter 2 merges into the shaft 22. This shaft 22 has a considerably smaller diameter than the head section of the adapter 2. It is desirable for this shaft 22 to be elastically flexible to a limited extent in the areas of highest loading.

At the lower end of the shaft 22 in this example there is a threaded section onto which the threaded bushing 23 can be screwed. The bushing 23 preferably has an external diameter corresponding to that of the shaft 22. The threaded bushing 23 also has, in its head area, a flange 231 acting as an axial stop 231. A suitable profile (slit 232) is used for turning the bushing 23 with the aid of an instrument.

This bushing 23 serves principally to configure the length of the shaft 22 within variable limits, without the shaft 22 protruding too far on the lateral side of the femur. The bushing 23 can also be made of a material permitting particularly good sliding, so that the support bearing 5 as far as possible does not have to take up any axial forces.

To prepare for introducing the adapter 2 into the head of the femur 1, a bore is first made for the shaft 22. This bore fixes the angle 16 between the axis 15 of the adapter 2 and the central longitudinal axis 14 of the femur.

After this bore has been made, a preferably approximately conical recess adapted to the support ring 3 is made, concentric to the axis 15, on the proximal side of the femur 1. The cone angle 30 of this recess can be different in the area of the recess. In the area of the proximal cortical substance 11, i.e. where the support ring 3 lies with its support surface 33 on the surface 111, this angle 30 is preferably chosen to be greater than 120°.

The preparation of this conical recess results, on the proximal cortical substance 11, in a bearing surface 111 which can take up forces parallel to the axis 15 and forces transverse to this axis 15. The lower part of the bearing surface 111 is of particular importance, the latter being able to take up forces acting in the longitudinal direction of the femur 1.

A conical support ring 3 of limited elasticity, and therefore with relatively thin walls (depending on the anticipated load) is inserted into this conical recess. This support ring 3 has a flange-like stop 31 which is offset outward and downward in relation to the bearing surface 111, i.e. offset in relation to the longitudinal axis 14 of the thigh bone, and on which the support shoulder 21 of the adapter 2 lies.

The bore 32 in immediate proximity to the stop 31, or another inner annular recess in the support ring 3, ensures radial centering of the adapter 2 in the support ring 3. The bore 32 offset laterally in the support ring 3 ensures that, in the event of considerable radial loads, the support ring 3 at all times bears on the entire surface 111 of the cortical substance 11.

An enlarged bore is also arranged, coaxial to the axis 15, on the outer or lateral cortical substance 12 and receives the support bearing 5. This bore is expediently oriented at right angles to the central outer contour of the cortical substance 12 in this area, so that the flat flange 53 of the support bearing 5 has the best possible contact on the cortical substance 12.

In the simplest case, the support bearing 5 is introduced into the bore with a press-fit. If the contact surface of the support bearing 5 on the lateral cortical substance 12 is made slightly concave, it is possible to reduce the contact forces on the cortical substance 12 in the inserted state while maintaining good positional stability of the support bearing 5.

In the central area, this support bearing 5 has a bore 52 whose axis is aligned with the axis 15 of the shaft 22.

It has proven expedient either to design this bore 52 with a dome shape or to provide a sort of ball joint (61, 62 —in FIG. 5) at this point, so that the in most cases unavoidable angle 51 or 63 between the axis of the bore in the outer cortical substance 12 and the axis 15 of the adapter 2 can be compensated.

This bore 52 can guide the shaft 22' with a form-fit either directly or via a threaded bushing 23 secured on the shaft 22.

The adapter 2 is now introduced from the proximal direction into the head of the femur 1 equipped with the support ring 3 and the support bearing 5 (6) and—if so desired—is axially secured (not braced!!!) from outside and from below by attaching the threaded bushing 23.

The force F generally acting on the joint ball 20 (the direction of the force is variable within limits) is taken up, via the support shoulder 21 and the bearing surface 111 on the cortical substance 11, which surface is conical with respect to the axis 15, by those parts of the femur 1 which have the highest strength, namely by the cortical substance 11. Bracing inside the femur is completely excluded.

To avoid extreme peak loads, in particular between the support ring 3 and the bearing surface 111, it is expedient to arrange elastic elements between the ball 20 of the joint and the bearing surface 111.

A certain amount of elasticity is in this case already afforded by the relatively thin-walled support ring 3. It is possible to further adapt the extent of the compliance to the physique of the particular patient by arranging radial slits 34 in the support ring 3, for example as is shown in FIG. 2. These slits 34 permit a greater or lesser elasticity, particularly in the area of the support surface 33, relative to the stop 310 on the support shoulder 21.

Additional elasticity is ensured by the relatively small diameter of the shaft 22 on the adapter 2. By means of the normal loading—indicated by the arrow F—via the axis of the ball 20 and the resistance of the support bearing 5, the force acting on the support shoulder 21 from below effects a slight bending of the adapter 2 about the contact point of the radial bearing in the bore 32 near the support shoulder 21. By means of said elastically configured elements, the femoral neck endoprosthesis as a whole acquires an elasticity similar to that of a healthy femur 1.

A further advantage of this femoral neck endo-prosthesis is that the very narrow areas of the cortical substance 11, 12 in which the forces are passed into the femur 1 are supplied with body fluid from inside via the spongy substance 13 or are supplied from the outside with function-preserving material. Disintegration of the cortical substance 11, 12 in these limited areas of loading need not therefore be feared, even when the prosthesis is used for a long time.

Figure 3:
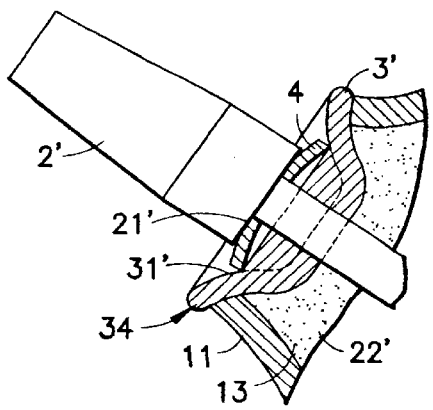
FIG. 3 shows a second alternative embodiment of a femoral neck endoprosthesis.

A further illustrative embodiment of the femoral neck endoprosthesis is shown in FIG. 3. The construction of this prosthesis in the area of the support ring 3 and in the area of the support bearing 5 is identical or similar to the example which was described with reference to FIG. 1.

As far as its outermost end, the shaft 22' of the adapter 2 in this case has the same diameter and has no thread. It slides directly in the bore 52 of the support bearing 5. The bore 52 is slightly dome-shaped here, so that small angle deviations 51 can be corrected.

In this alternative embodiment, the shaft 22' is to be made available in a greater length before insertion. Its length is to be determined after preparations have been made for fitting the adapter 2 and is to be configured such that its free projection from the lateral side of the femur 1 is limited.

Figure 4:
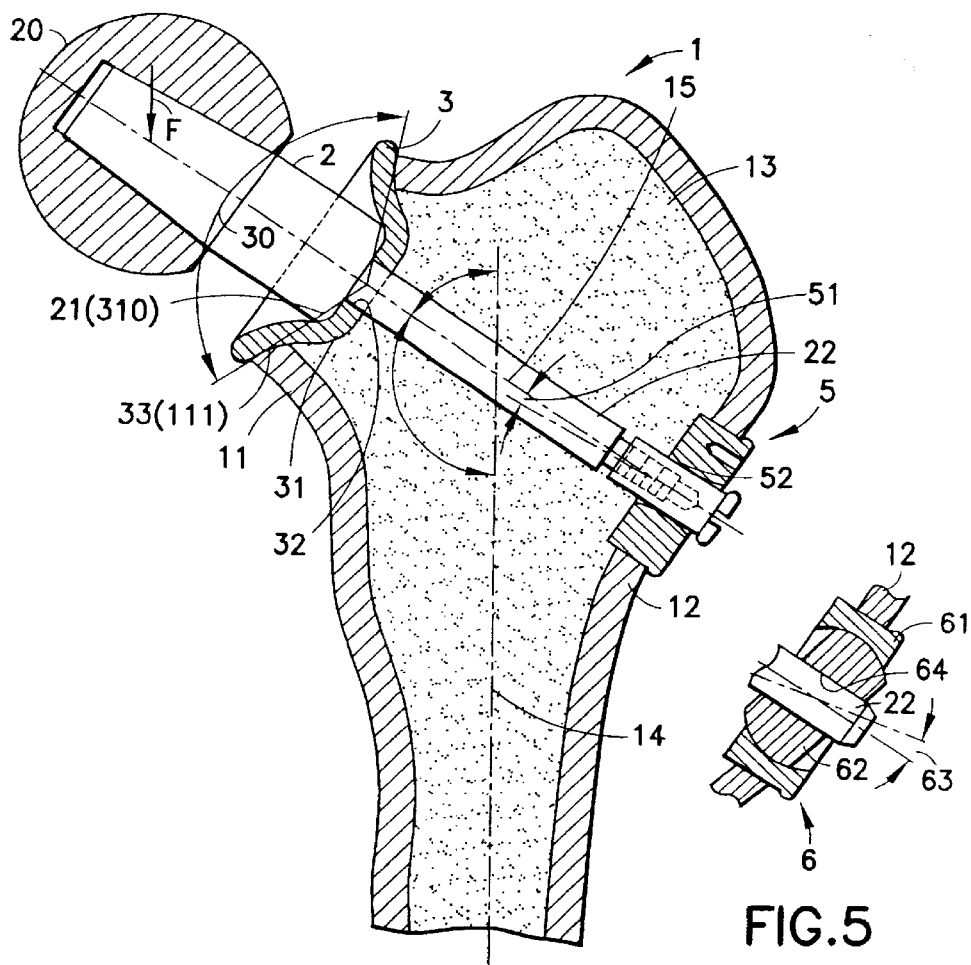
FIG. 4 shows a modification of the elastic configuration of a support ring.

FIG. 4 shows a further alternative embodiment for the elastic configuration of the support ring 3'. Here, the support shoulder 21' of the adapter 2' is offset toward the proximal side. Between this support shoulder 21' and the support ring 3', a spring ring 4 is fitted which can be provided with a slit. By virtue of the fact that the spring ring 4 bears in the inner cone of the support ring 3', it permits, in combination with a support ring 3' of limited elasticity, an additional elasticity in the axial direction and also transverse to this axis 15. The slightly longer shaft 22" of the adapter 2' ensures additional elasticity.

FIG. 5 shows an alternative embodiment of the support bearing 6 which can be used instead of the support bearing 5. The support bearing 6 fitted in this case into the outer cortical substance 12 consists of a guide ring 61 and a slide ring 62. The guide ring 61 is pressed into or engaged in the cortical substance 12 with a secure fit. On its inside, it has a concavely spherical surface into which the slide ring 62 can be inserted in an oscillating manner. The slide ring 62 has a central bore 64 which corresponds to the diameter of the shaft 22', 22" or to the diameter of the bushing 23. It permits adjustment to any desired angles 63 within limits.

The advantage of this design of the support bearing 6 is that the shaft 22' of the prosthesis can at all times be guided without bracing. Adaptation to the in most cases very different outer contours of the femur 1 and to different angles of the bores for the adapter 2 in the femur can at all times be ensured with a high degree of precision.

Figure 6:
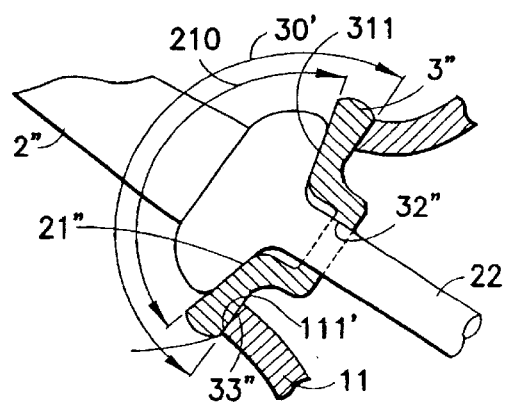
FIG. 6 shows a further advantageous embodiment of the support shoulder of the adapter and of the support ring.

The representation in FIG. 6 shows a particularly interesting embodiment of the invention. The support ring 3" lies on a plane surface 111' of the cortical substance 11. The support shoulder 21" of the adapter 2" is designed as a flat conical ring and bears on the likewise conical surface 31" on the flange of the support ring 3".

The bore 32" guides the shaft 22 of the adapter 2" with a slightly greater play, so that the centering of the adapter 2" takes place under normal conditions via the conical support shoulder 21" in conjunction with the conical stop surface 31" of the support ring 3".

Only in the event of excessive loading does the bore 32" act as a radial guide of the adapter 2". The radial force transmission from the support ring to the femur is in this case assisted by the transition to the hub of the support ring 3".

Thus, while there have been shown and described and pointed out fundamental novel features of the present invention as applied to a preferred embodiment thereof, it will be understood that various omissions and substitutions and changes in the form and details of the devices illustrated, and in their operation, may be made by those skilled in the art without departing from the spirit of the present invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature.

It is the intention, therefore, to be limited only as indicated by the scope of the claims appended hereto."

What is claimed is:

1. A femoral neck endoprosthesis for an artificial hip joint having a ball joint, comprising: an adapter for accommodating the joint ball; a support ring for axially and radially guiding the adapter on a proximal side of the femur; and a support bearing for guiding the adapter on a lateral side of the femur, the adapter having a support shoulder directed toward the femur and a shaft for penetrating the femur approximately along an extended axis of the femoral neck, the support ring for being mounted only on the proximal side of the femur, said support ring having a flange support surface for being mounted on a worked bearing surface of proximal cortical substance of the femur and a hub for being mounted inside the femur, the support ring further having an axial stop for the support shoulder of the adapter and a bore for the shaft of the adapter so as to guide the adapter, the bore being laterally offset in relation to the support surface, the support bearing for being fixed only on the lateral side of the femur, substantially on the lateral cortical substance, the support bearing having a guide bore for the shaft of the adapter, which guide bore has an active axis adjustable with the axis of the adapter.

2. A femoral neck endoprosthesis as defined in claim 1, wherein the adapter has a conical support shoulder which matches a conical stop surface on the flange of the support ring, the shaft of the adapter being guided in the bore of the support ring with play.

3. A femoral neck endoprosthesis as defined in claim 1, wherein the support surface of the support ring has, with respect to the axis of the adapter, a central cone angle of between 120° and 160° opening in a proximal direction.

4. A femoral neck endoprosthesis as defined in claim 1, wherein the support ring, between bearing surfaces of the support shoulder and the support surface, is designed with limited elasticity toward the bearing surface of the proximal cortical substance.

5. A femoral neck endoprosthesis as defined in claim 1, wherein the flange of the support ring has at least one slit on its circumference.

6. A femoral neck endoprosthesis as defined in claim 5, wherein the slit is a radial slit.

7. A femoral neck endoprosthesis as defined in claim 1, wherein the support ring has a substantially nonelastic inner conical flange, and further comprising an at least axially elastic spring ring arranged between the support shoulder of the adapter and an inner cone of the conical flange.

8. A femoral neck endoprosthesis as defined in claim 1, wherein the support bearing is configured to penetrate the lateral cortical substance of the femur substantially perpendicular to a surface of the lateral cortical substance and with a form-fit, the bore of the support bearing having an axis inclined in relation to an axis of the support bearing by an angle of between 5° and 30°.

9. A femoral neck endoprosthesis as defined in claim 1, wherein the support bearing has profiles for turning the support bearing in the cortical substance, the bore being aligned with a probable position of the axis of the shaft of the adapter and having a dome shape.

10. A femoral neck endoprosthesis as defined in claim 1, Wherein the support bearing has an outer guide ring with a spherical inner guide surface and a spherical slide ring fittable in the guide ring and has the bore for the shaft of the adapter.

11. A femoral neck endoprosthesis as defined in claim 1, and further comprising: a detachable axial bearing assigned to an outer end of the shaft.

12. A femoral neck endoprosthesis as defined in claim 11, wherein the axial bearing is a threaded bushing having an external diameter that penetrates the bore in the support bearing with play, the threaded bushing having axially directed stops on an outer side and having a screw connection at the outer end of the shaft so that the threaded bushing is axially adjustable, the threaded bushing being fixable in an adjusted position.

* * * * *